(12) United States Patent
Wang et al.

(10) Patent No.: US 8,920,165 B2
(45) Date of Patent: Dec. 30, 2014

(54) SELF-LOCKING AND POSITIONING DEVICE FOR DENTAL BRACE

(71) Applicant: Micro Art Technology Co., Ltd., Hsinchu (TW)

(72) Inventors: Cheng-Hsien Wang, Hsinchu (TW); Kuo-Li Wu, Hsinchu (TW); Ming-Hsun Yang, Hsinchu (TW); Hsi-Yao Wu, Hsinchu (TW)

(73) Assignee: Micro Art Technology Co., Ltd., Hsinchu (TW)

( * ) Notice: Subject to any disclaimer, the term of this patent is extended or adjusted under 35 U.S.C. 154(b) by 0 days.

(21) Appl. No.: 13/910,253

(22) Filed: Jun. 5, 2013

(65) Prior Publication Data

US 2013/0330683 A1     Dec. 12, 2013

(30) Foreign Application Priority Data

Jun. 8, 2012 (TW) .............................. 101211149 U

(51) Int. Cl.
*A61C 7/30* (2006.01)
*A61C 7/28* (2006.01)

(52) U.S. Cl.
CPC .. *A61C 7/287* (2013.01); *A61C 7/30* (2013.01)
USPC ............................................... 433/11; 433/10

(58) Field of Classification Search
USPC ........................................................ 433/10, 11
See application file for complete search history.

(56) References Cited

U.S. PATENT DOCUMENTS

| 5,094,614 A * | 3/1992 | Wildman .......................... 433/14 |
| 5,322,435 A * | 6/1994 | Pletcher ........................... 433/11 |
| 5,613,850 A * | 3/1997 | Wildman et al. ................ 433/10 |
| 7,419,375 B2 * | 9/2008 | Farzin-Nia et al. .............. 433/10 |
| 7,704,072 B2 * | 4/2010 | Damon ............................ 433/11 |
| 8,251,696 B2 * | 8/2012 | Rodriguez et al. .............. 433/10 |
| 2009/0004619 A1 * | 1/2009 | Oda et al. ......................... 433/24 |
| 2009/0155734 A1 * | 6/2009 | Damon ............................ 433/10 |

* cited by examiner

*Primary Examiner* — Ralph Lewis
(74) *Attorney, Agent, or Firm* — Rosenberg, Klein & Lee

(57) ABSTRACT

A self-locking and positioning device for a dental brace, comprising: a brace main body, an elastic piece, and an upper cover. Wherein, on the brace main body is provided with a track and a fixing slot, while on the elastic piece is provided with a positioning piece and a slot. The positioning piece is provided with a barb, while the upper cover slides and fixes into the brace main body through the track. Then, the barb of the positioning piece on the elastic piece will act against a block portion on bottom of said upper cover, to restrict movement of the upper cover, to lock automatically the upper cover into position. The dental brace is simple in construction and easy to assemble, hereby raising production efficiency and yield.

12 Claims, 4 Drawing Sheets

SELF-LOCKING AND POSITIONING DEVICE FOR DENTAL BRACE

BACKGROUND OF THE INVENTION

1. Field of the Invention

The present invention relates to a positioning mechanism for a dental brace, and in particular to a self-locking and positioning device for a detachable dental brace.

2. The Prior Arts

Along with the raise of living standard and quality of life, people are paying more attention to their appearances. To have healthy, nice-looking, and well functioning teeth, dentition, and face, is essential to and very helpful in broadening social circles, increasing job opportunities, and enhancing self confidence. Therefore, tooth correction, dentition correction, and orthodontic treatment are getting very popular, to provide dental health required, and at the same time, encourage a person to make a pretty smile, to be shared with other people.

The conventional tooth correction and therapy require use of steel wires or rubber band to fix the correction line onto the dental brace. However, this could cause discomfort to the taste of the user, since his mouth is full of taste of rubber band. Later research develops a self-locking mechanism for a metal self-locking brace. Wherein, the brace main body and the upper cover are formed into a body, without the need of a rubber band. However, the mold required in this process is complicated, and its size is not easy to control; therefore, the yield is low, the mechanism is weak in construction, and is liable to be damaged during usage. Moreover, for different users, the tooth shapes are different, such that the brace requires different slot width, as such it would require to make modes of different sizes. In this respect, another type of slide cover brace is proposed, such as a Damon2 detention brace. Wherein, a built-in slidable open-close upper cover is designed to dispose on the slot of the brace main body, so as to fix the correction line into the slot. In addition, the upper cover is locked into position on the brace main body. Since unlike the previous approach of fixing the correction line onto the brace, the slidable cover brace allows the correction line to slide freely in the brace, so that the user feels more comfortable during the therapy, and the period of therapy is shortened. Yet for different slot width, the sliding cover brace still requires to provide various sizes of brace main body. Besides, the locking of the upper cover is less reliable, and is liable to slide open or burst open.

Therefore, presently, the design and performance o the dental brace is not quite satisfactory, and it has much room for improvement.

SUMMARY OF THE INVENTION

In view of the problems and drawbacks of the prior art, the present invention provides a self-locking and positioning device for a dental brace, to effectively overcome the shortcomings of the prior art.

A major objective of the present invention is to provide a self-locking and positioning device for a dental brace. Wherein, an elastic piece and a detachable upper cover are placed on the dental brace. One end of the elastic piece is fixed onto the fixing slot of the brace main body; while the other end is disposed on a track, and is provided with a barb, so that after the upper cover is slid in from the track, it is hooked by the barb into a locking position. Therefore, it is simple in construction, and easy to assemble.

Another objective of the present case is to provide a self-locking and positioning device for a dental brace, to reduce the structure complexity of the brace main body and the upper cover, and to raise the effectiveness and yield of the mold.

A further objective of the present case is to provide a self-locking and positioning device for a dental brace, having the advantages of simple in construction and easy to produce, so that the elastic piece may change width of the slot, but it uses the same brace main body for different dental brace to save cost.

In order to achieve the above mentioned objective, the present invention provides a self-locking and positioning device for a dental brace, including: a brace main body, an elastic piece, and an upper cover. Wherein, on the brace main body is provided with a track and a fixing slot; while on the elastic piece is provided with a positioning piece and a slot, so that the upper cover is able to slide and fix into the brace main body from the track, and the positioning piece on the elastic piece is able to restrict movement of the upper cover, to automatically lock the elastic piece into position, so that it can not move.

Further scope of the applicability of the present invention will become apparent from the detailed descriptions given hereinafter. However, it should be understood that the detailed descriptions and specific examples, while indicating preferred embodiments of the present invention, are given by way of illustration only, since various changes and modifications within the spirit and scope of the present invention will become apparent to those skilled in the art from this detailed descriptions.

BRIEF DESCRIPTION OF THE DRAWINGS

The related drawings in connection with the detailed descriptions of the present invention to be made later are described briefly as follows, in which.

DETAILED DESCRIPTION OF THE PREFERRED EMBODIMENT

The purpose, construction, features, functions and advantages of the present invention can be appreciated and understood more thoroughly through the following detailed description with reference to the attached drawings.

Figure 1:
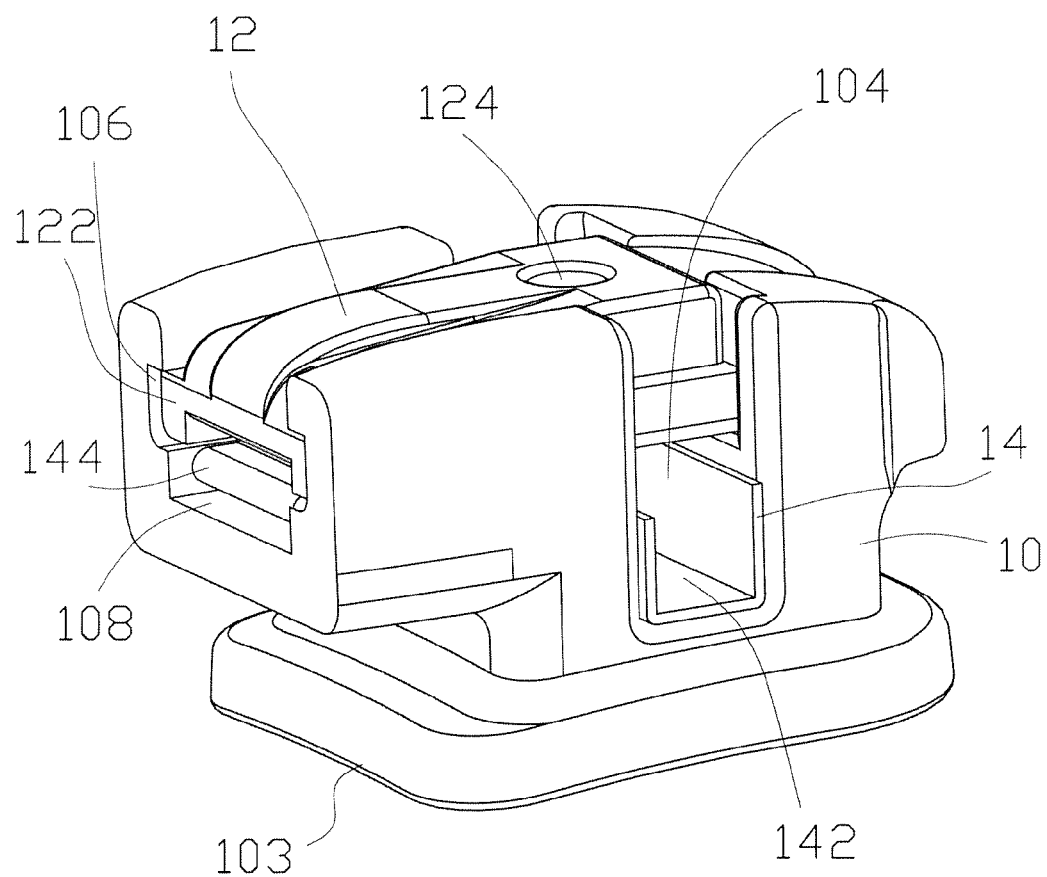
FIG. 1 is a perspective view of a self-locking and positioning device for a dental brace according to the present invention.
Figure 2:
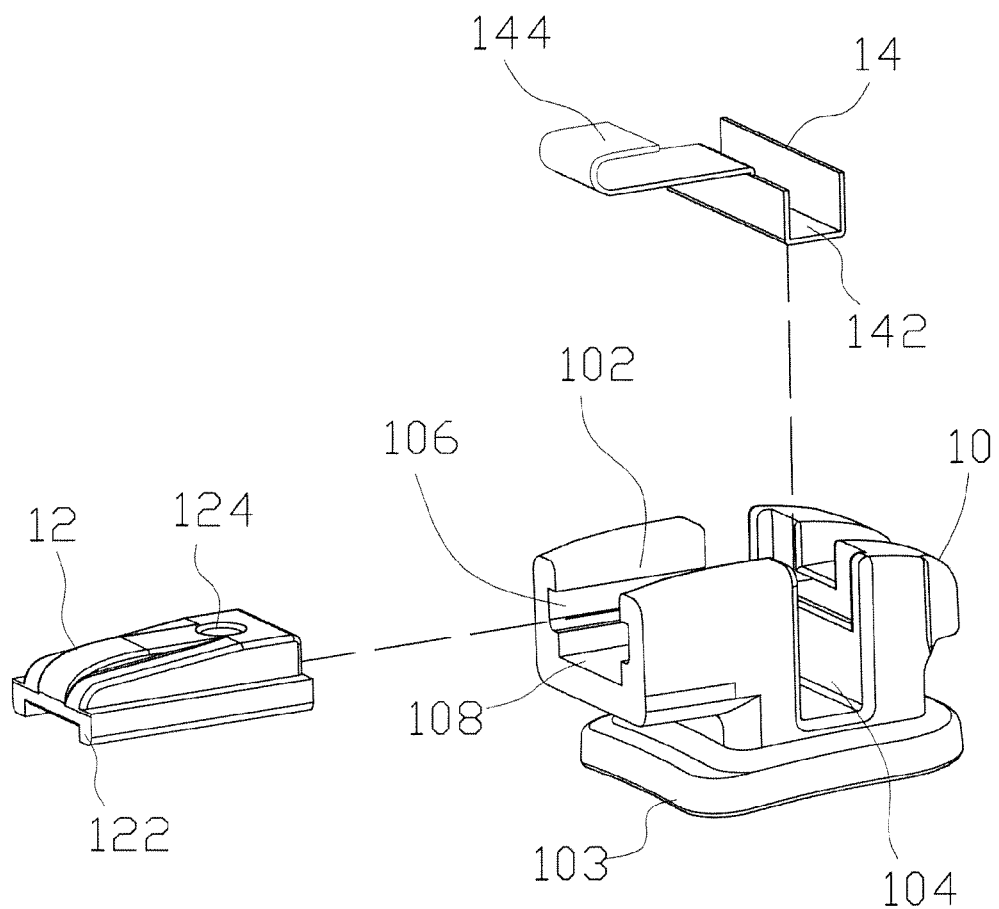
FIG. 2 is an exploded view of a self-locking and positioning device for a dental brace according to the present invention.

The present invention provides a self-locking and positioning device for a dental brace. Refer to FIGS. 1 and 2 respectively for a perspective view and an exploded view of a self-locking and positioning device for a dental brace according to the present invention.

As shown in FIGS. 1 and 2, the self-locking and positioning device for a dental brace includes: a brace main body 10, an upper cover 12, and an elastic piece 14. Wherein, the brace main body 10 is roughly a tetragon in shape, including a base 103, a track 102, and a fixing slot 104, with the track 102 and the fixing slot 104 both located on the base 103. The orientations of the track 102 and the fixing slot 104 are perpendicular to each other, and the base 103 is glued onto the surface of the teeth of the user. The elastic piece 14 is made of metal, plastic, or other polymers, with a thickness of 0.01 to 0.5 cm. On the elastic piece 14 is provided with a positioning piece 144 and a slot 142. The slot 142 is a block portion of a long strip shape, and is disposed in the fixing slot 104 of the brace main body 10, such that the correction wire passes over the fixing slot 104. The positioning piece 144 is placed into a receiving space 108 below the track 102. One end of the positioning piece 144 is connected to the slot 142, while other end is bent into a barb. The upper cover 12 can be slid and fixed in the brace main body 10 through the track 102. The positioning piece 144 of the elastic piece 14 is fastened to the bottom of the upper cover 12, to lock the elastic piece 14 automatically into position, so it can not move.

On both sides inside the track 102 are provided each with an indent portion 106, and on both sides below the upper cover 12 is each extended a protrusion portion 122 of a long strip shape, so that the protrusion portion 122 of the upper cover 12 and the indent portion 106 of the track 102 may match and engage each other. Therefore, the upper cover 12 utilizes the protrusion portion 122 to fasten into the indent portion 106 of the track 102.

Figure 3A:
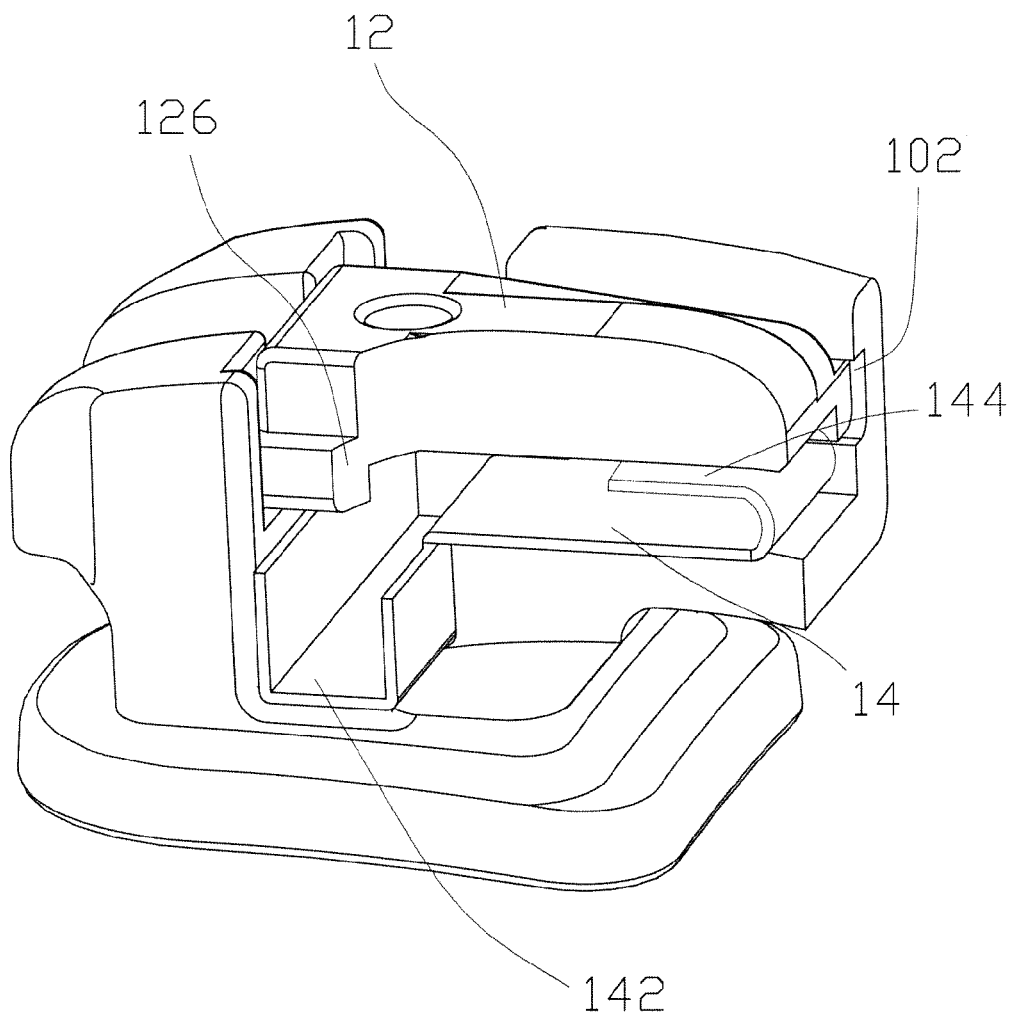
FIGS. 3A and 3B are the perspective views of a self-locking and positioning device for a dental brace according to the present invention, with FIG. 3A showing that the upper cover is closed, while FIG. 3B showing that the upper cover is open.
Figure 3B:
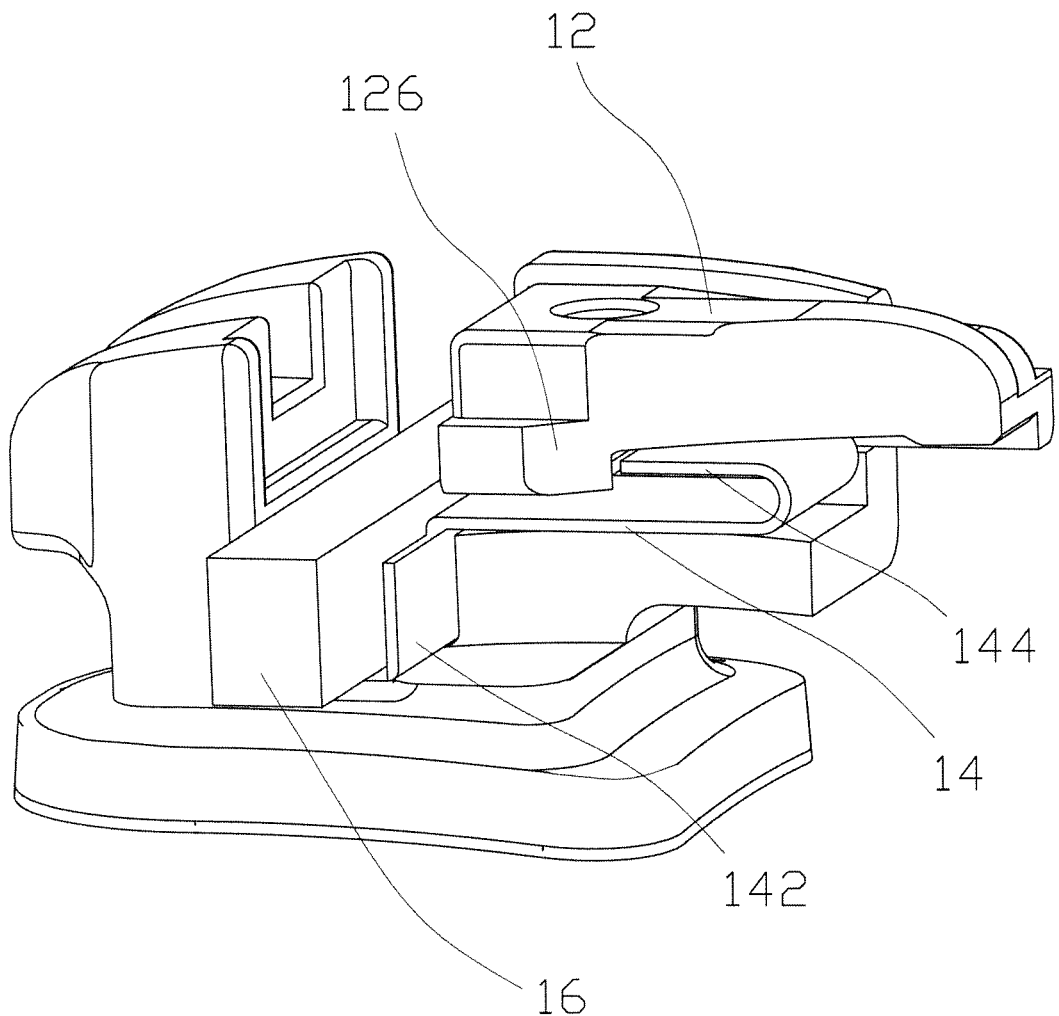

Refer to FIGS. 3A and 3B for the perspective views of a self-locking and positioning device for a dental brace according to the present invention, with FIG. 3A showing that the upper cover is closed, while FIG. 3B showing that the upper cover is opened. As shown in FIGS. 3A and 3B, the bottom of the upper cover 12 is provided with a block portion 126, and the positioning piece 144 is bent into a barb. When the upper cover 12 is opened, the block portion 126 is acted against by the positioning piece 144, thus it can not move further, so that the upper cover 12 can not be detached from the track 102 backward along the original route. At this time, the correction line 16 is placed into the slot 142.

On the upper cover 12 is provided with a fixing hole 124. When the upper cover 12 is fastened into the track 102, the fixing hole 124 is located right above the slot 142.

In the application of the present invention, the base of the brace main body is fixed onto the surface of user's teeth, and the elastic piece is placed onto the brace main body, so that the slot is in the fixing slot, and the positioning piece is in the track. Then, the upper cover is fastened onto the brace main body along the track, the barb of the positioning piece will act against the block portion on the bottom of the upper cover, so that the upper cover can not move, in achieving self-locking and positioning functions, while the correction line passes through the slot.

Summing up the above, the present invention provides a self-locking and positioning device for a dental brace, which utilizes the block portion on the bottom of the upper cover and the barb of the positioning piece, to lock into position. The present invention is simple in construction and easy in assembly, and is capable of raising production efficiency and yield. The advantage of simple construction allows the elastic piece to vary the width of the slot, while using the same brace main body, for various different dental braces to be used, without the need to produce brace main bodies of various sizes, in achieving significant saving of cost.

The above detailed description of the preferred embodiment is intended to describe more clearly the characteristics and spirit of the present invention. However, the preferred embodiments disclosed above are not intended to be any restrictions to the scope of the present invention. Conversely, its purpose is to include the various changes and equivalent arrangements which are within the scope of the appended claims.

What is claimed is:

1. A self-locking and positioning device for a dental brace having a correction line defining an archwire, comprising:
a brace main body having a track and a fixing slot;
an elastic piece having a positioning piece portion and a slotted portion, said slotted portion having a U-shaped profile selectively sized to accommodate differently sized archwires and being inserted into said fixing slot of said brace main body for receiving therein and partially encompassing the correction line of the dental brace, said positioning piece portion defining an elastic hook portion extending substantially perpendicular to a sidewall of said slotted portion; and
an upper cover, slideably engageable with said track of said brace main body to form a closure over said fixing slot and lock said elastic piece into position, said elastic hook portion for releasably engaging with a shoulder formed in said upper cover.

2. The self-locking and positioning device for a dental brace as claimed in claim 1, wherein orientations of said track and said fixing slot are perpendicular to each other.

3. The self-locking and positioning device for a dental brace as claimed in claim 1, wherein on both sides of said upper cover are each provided with a long strip shaped protrusion portion, on both sides inside said track of said brace main body is provided with an indent portion, so that said two protrusion portions of said upper cover slide into said brace main body along said two indent portions of said track.

4. The self-locking and positioning device for a dental brace as claimed in claim 3, wherein below said two indent portions is a receiving space, and said positioning piece portion of said elastic piece is placed in said receiving space, then, said upper cover is slid into said track, so that said upper cover is located above said positioning piece portion and said slotted portion.

5. The self-locking and positioning device for a dental brace as claimed in claim 1, wherein said slotted portion is of a long strip shape, one end of said positioning piece portion is connected to said slotted portion, while other end is bent into a barb shape.

6. The self-locking and positioning device for a dental brace as claimed in claim 5, wherein bottom of said upper cover is provided with a block portion, such that when said upper cover is opened, said positioning piece portion of barb shape is pressed against said block portion, so that said upper cover stop moving.

7. The self-locking and positioning device for a dental brace as claimed in claim 1, wherein the correction line passes through said slotted portion while disposed in said fixing slot.

8. The self-locking and positioning device for a dental brace as claimed in claim 1, wherein a fixing hole is provided in said upper cover.

9. The self-locking and positioning device for a dental brace as claimed in claim 1, wherein said brace main body further includes a base, said track and said fixing slot are both placed on said base, such that said base is glued onto surface of teeth of a user.

10. The self-locking and positioning device for a dental brace as claimed in claim 1, wherein said elastic piece is made of metal, plastic, and other polymers.

11. The self-locking and positioning device for a dental brace as claimed in claim 1, wherein said elastic piece is selected to have a thickness sized to fill a space between the correction line and side walls of said fixing slot.

12. The self-locking and positioning device for a dental brace as claimed in claim 11, wherein said selected elastic piece has a thickness in a range of 0.01 to 0.5 cm.

\* \* \* \* \*